(12) United States Patent
Mukherjee et al.

(10) Patent No.: US 7,672,987 B2
(45) Date of Patent: Mar. 2, 2010

(54) SYSTEM AND METHOD FOR INTEGRATION OF MEDICAL INFORMATION

(75) Inventors: Saikat Mukherjee, North Brunswick, NJ (US); Amit Chakraborty, East Windsor, NJ (US)

(73) Assignee: Siemens Corporate Research, Inc., Princeton, NJ (US)

( * ) Notice: Subject to any disclaimer, the term of this patent is extended or adjusted under 35 U.S.C. 154(b) by 212 days.

(21) Appl. No.: 11/419,789

(22) Filed: May 23, 2006

(65) Prior Publication Data

US 2006/0271556 A1    Nov. 30, 2006

Related U.S. Application Data

(60) Provisional application No. 60/684,370, filed on May 25, 2005.

(51) Int. Cl.
   *G06F 17/30*    (2006.01)
(52) U.S. Cl. .................................................... 707/776
(58) Field of Classification Search ....................... None
See application file for complete search history.

(56) References Cited

OTHER PUBLICATIONS

Bodenreider, "The Unified Medical Language System (UMLS): integrating biomedical terminology", Nucleic Acids Research, 2004, vol. 32, Database issue D267-D270.*

Doan, AnHai et al., "Reconciling Schemes of Disparate Data Sources: A Machine-Learning Approach," *Department of Computer Science and Engineering University of Washington*, Settle WA 98195, ACM SIGMOD (2001).

Doan, Anhai et al., "Learning to Map between Ontologies on the Semantic Web," *Computer Science and Engineering University of Washington*, Seattle, WA. USA WWW (2002).

Ciravegna, Fabio, "Adaptive information Extraction from Text by Rule Induction and Generalisation," *Department of Computer Science University of Sheffield*.

McCallum, Andrew, "Improving Text Classification by Shrinkage in a Hierarchy of Classes."

Schapire, Robert E., "A Brief Introduction to Boosting."

* cited by examiner

*Primary Examiner*—Kavita Padmanabhan

(57) ABSTRACT

A computer system for integrating medical information using the Unified Medical Language System (UMLS) as a taxonomy of medical terms includes a learner module for learning from training data concept classifiers for a source ontology and a target ontology, a mapper module for generating associations between source and target ontology classifiers using the UMLS, an annotator module for extracting knowledge from test data using source and target ontology classifiers and UMLS, and a feedback module for ranking associations according to a level or certainty, and presenting those associations that fall below a predefined level of certainty to a user for correction.

10 Claims, 7 Drawing Sheets

SYSTEM AND METHOD FOR INTEGRATION OF MEDICAL INFORMATION

CROSS REFERENCE TO RELATED UNITED STATES APPLICATION

This application claims priority from "Medina—Medical Information Integration", U.S. Provisional Application No. 60/684,370 of Mukherjee, et a., filed May 25, 2005, the contents of which are incorporated herein by reference.

TECHNICAL FIELD

This invention is directed to the representation and integration of digitized medical information.

DISCUSSION OF THE RELATED ART

Vast amounts of biomedical data are being generated by diverse sources at a rapid rate, in addition to the data being produced by legacy systems still in place. Examples of this information include clinical laboratory test results, physician reports, and genomic and proteomic data. The nature of this data spans an entire spectrum from images to unstructured text to structured tables. Future advances in medical informatics depend on harnessing the power of this information. For instance, the vision of personalized healthcare depends on being able to associate test reports with physician notes and omics data for every individual. Due to the enormous quantity of data being generated, developing automated techniques for analyzing the data is important to the realization of next-generation health care services.

The success of automated techniques for analyzing biomedical data depends on the representation of the data in machine-readable formats. However, it is seldom the case that the data being generated by different providers is in such a desired format. Integration is made more difficult by providers following their own individual data representation schemes, which results in extremely heterogeneous content. Due to this heterogeneity, information from different providers can be integrated into common frameworks only with a great degree of manual effort. Thus, there is a desire for developing automated techniques for integrating unstructured and heterogeneous content into a standardized structured format in medical informatics.

Researchers have addressed these needs by proposing solutions for information integration both within the medical informatics community as well as part of general database research. Proposed solutions for information integration can be broadly classified into either federated approaches or mediator-based approaches.

The federated or warehouse-based approach integrates data from diverse sources into a central repository. Wrappers, or information extraction techniques, have been primarily used for such warehousing. Wrapper-based solutions are characterized by the use of extraction expression rules which are either manually created or learned from labeled examples. Designed mainly for semi-structured content, wrapper-based techniques have also been augmented with natural language processing capabilities for application on grammatically correct unstructured content. However, medical informatics data is frequently in an unstructured but not a sentential format. This makes the application of wrapper-based techniques for such data difficult. Furthermore, the use of heavy-weight natural language processing methods in unstructured data integration raises questions about the scalability of the existing techniques.

The mediator-based approach, on the other hand, attempts to integrate data by generating mappings between the schemas of the local sources and a common global schema. Queries on the global schema are translated on the fly to queries on the local schemas for data retrieval. These approaches work when data is described in terms of well-defined relational or semi-structured schemas. It is not clear how these techniques can be applied to schema-less unstructured data, which is often the case in medical informatics.

The medical domain is uniquely characterized by the presence of not only diverse sources, each following their own information representation schemas, but also by varying degrees of structure in the content ranging from relational tables to unstructured text. For instance, physician notes represent one end of this spectrum, which might have complete unstructured text sentences, while laboratory test results are frequently unstructured text with no sentential structure. On the other hand, drug information from pharmaceutical enterprises is often in structured relational tables. Thus, a complete information integration solution has to incorporate ideas from both wrapper-based federated approaches as well as schema-mapping mediator techniques.

Recent federated and mediator-based approaches exploit a variety of additional information while performing the extraction or mapping respectively. Such additional information typically comes from ontologies, which are formalizations of domain knowledge. Usually, ontologies are taxonomies of domain concepts associated with terminological vocabularies (or concept instances). The goal in a federated approach is to structure the data with respect to the ontology. To this end, the ontology's vocabulary is used to learn statistical models for identifying concept instances in the unstructured data. In a mediator-based approach, data instances associated with the local schemas are used to learn statistical models of schema elements, which are then used to measure similarities between elements from different sources. Additionally, domain information is also used to constrain later stages in the extraction or mapping process. However, in these learning-based approaches, generating precise mappings or extractions require significant effort in the training phase. Hence, techniques which combine limited training based learning algorithms with domain information have the potential to offer scalable solutions to the information integration problem.

SUMMARY OF THE INVENTION

Exemplary embodiments of the invention as described herein generally include methods and systems for medical information integration, which combine limited training machine-learning algorithms, knowledge bases, and user feedback for a scalable and automated solution to the medical information integration problem. A method and system according to an embodiment of the invention combines the scalability of learning methods with the richness of domain knowledge for a holistic solution to the integration problem. A system according to an embodiment of the invention includes a mapping as well an extraction component which make use of the Unified Medical Language System (UMLS) as the source of global medical knowledge. Both the mapping and the extraction components are driven by a learning module that makes use of (1) the hierarchical structure of ontologies to improve the learners by using the statistical technique of shrinkage; (2) multiple instance learning techniques for handling ambiguity in the training data; and (3) boosting to enhance the performance of the base learners. During knowledge extraction, hierarchical classification of the test data is performed with respect to the UMLS and the target ontology. Relevance feedback is incorporated into the system for user corrections of ambiguous mapping and extractions.

According to an aspect of the invention, there is provided a system for integrating medical information using the Unified Medical Language System (UMLS) as a taxonomy of medical terms, said system implemented by a program of instructions executable by a computer that are tangibly embodied in one or more computer readable program storage devices, said system including a learner module adapted to learning from training data concept classifiers for a source ontology and a target ontology, wherein an ontology is a formalizations of domain concepts associated with a medical terminological vocabulary, a mapper module adapted to generating associations between said source and target ontology classifiers using the UMLS, an annotater module adapted to extracting knowledge from test data using said source and target ontology classifiers and said Unified Medical Language System, and a feedback module adapted to ranking associations according to a level or certainty, and presenting those associations that fall below a predefined level of certainty to a user for correction.

According to a further aspect of the invention, the annotator module uses said classifier associations generated by said mapper module in the absence of a mapping from said target classifier ontology to UMLS.

According to a further aspect of the invention, the system comprises a knowledge database for storing said concept classifiers, and a mapping database for storing said associations between said classifiers.

According to a further aspect of the invention, the learner module is adapted to using multiple instance learning for modeling training data for those concepts that contain words with a varying degrees of relevance.

According to a further aspect of the invention, the learner module is adapted to using shrinkage of class hierarchy for refining parameters of lower level UMSL concepts using values from higher level UMSL concepts.

According to a further aspect of the invention, the learner module is adapted to using naïve Bayesian classifiers weak learners of said classifiers.

According to another aspect of the invention, there is provided a method for integrating medical information using the Unified Medical Language System (UMLS) as a hierarchical tree-structured taxonomy of medical terms, the method including providing a source ontology and a target ontology, said ontologies comprising formalizations of domain concepts associated with a medical terminological vocabulary, each concept being associated with data, learning concept classifiers for said source and target ontologies from training data, forming associations that map elements between the source and target ontology using the UMLS and said concept classifiers, ranking said associations in terms of a number of source and target concepts to which each UMLS concept is mapped, and presenting a predefined number of highest ranked associations to a user.

According to a further aspect of the invention, learning classifiers incldues the steps of providing an ontology, starting from a root concept of said ontology, collecting training data for said concept of said ontology by aggregating said training data from all descendants in the ontology tree, using multiple instance learning to learn a Naïve Bayes classifier for said concept, improving the classifier by using shrinkage along a path from the root of the ontology to said concept, and associating the learned classifier to the concept, wherein said steps of collecting training data, using multiple instance learning improving the classifier, and associating the learned classifier to the concept are repeated for each concept in the ontology.

According to a further aspect of the invention, the ontology is UMLS.

According to a further aspect of the invention, the ontology is the target ontology.

According to a further aspect of the invention, the ontology is the source ontology.

According to a further aspect of the invention, forming associations includes the steps of providing an ontology, initializing a test concept with a root concept of said ontology, initializing a current UMLS concept with a root concept of UMLS, classifying said test concept using the data associated with said test concept against all UMLS concepts at the hierarchy level of said current concept, selecting a best UMLS concept from said hierarchy level that has a best classification of said test concept, determining whether the data associated with said test concept can be better classified with any child concept of said best UMLS concept, and if said test concept cannot be better classified with any child concept of said best UMLS concept, associating said test concept to said best UMLS concept.

According to a further aspect of the invention, if said test concept can be better classified with a child concept of said best UMLS concept, reinitializing the current UMLS concept with said child UMLS concept that better classifies the data associated with said test concept, and repeating said steps of classifying said test concept, selecting a best UMLS concept, and determining whether the test data can be better classified with a child concept until either said current UMLS concept is a leaf UMLS concept or said test concept cannot be better classified to any children of the current UMLS concept.

According to a further aspect of the invention, the method comprises reinitializing said test concept to another concept in said ontology, and repeating said steps of initializing a current UMLS concept, classifying said test concept, selecting a best UMLS concept, and determining whether the test data can be better classified with a child concept until said test concept can be associated to a best UMLS concept.

According to a further aspect of the invention, the ontology is the target ontology.

According to a further aspect of the invention, the ontology is the source ontology.

According to a further aspect of the invention, ranking said associations includes the steps of determining, for each concept in UMLS, a product of a number of source ontologies and a number of target ontologies to which said UMLS concept is mapped by an association; and sorting said UMLS concepts in terms of decreasing product values, wherein said predefined number UMLS concepts with highest product values are selected.

According to a further aspect of the invention, the method comprises the step of retraining those classifiers presented to said user that are selected by said user for correction.

According to another aspect of the invention, there is provided a method for integrating medical information using the Unified Medical Language System (UMLS) as a hierarchical tree-structured taxonomy of medical terms, the method including providing a source ontology and a target ontology, said ontologies comprising formalizations of domain concepts associated with a medical terminological vocabulary, learning concept classifiers for said source and target ontologies from training data, extracting knowledge using the UMLS and said target ontology classifiers to annotate test data with UMLS and target ontology concepts, determining the probability of a test data item of being an instance of each concept of said target ontology, wherein if a difference between probability values for a best and a second best concepts is above a predefined threshold, storing said test data annotations in a database.

According to a further aspect of the invention, if the difference between probability values for the best and the second best concepts is below said predefined threshold, presenting said concept classifier to a user.

According to a further aspect of the invention, the method comprises the step of retraining those classifiers selected by said user for correction.

According to a further aspect of the invention, the method comprises forming associations that map elements between the target ontology and the UMLS using said concept classifiers.

According to a further aspect of the invention, extracting knowledge includes the steps of providing associations that map elements of the target ontology and UMLS, selecting a current UMLS hierarchy level that is a highest level that has been mapped to said target ontology, classifying all test data associated with those target ontology concepts that have been mapped to UMLS concepts in the current UMLS hierarchy level, selecting a best UMLS concept from said hierarchy level that has a best classification of said test data, determining whether said test data can be better classified with any child concept of said best UMLS concept, and if said test concept cannot be better classified with any child concept of said best UMLS concept, annotating said test concept with said best UMLS concept.

According to a further aspect of the invention, if said test data can be better classified with a child concept of said best UMLS concept, selecting a new current UMLS concept as said child UMLS concept level, and repeating said steps of classifying said test concept, selecting a best UMLS concept, and determining whether the test data can be better classified with a child concept until either said current UMLS concept is a leaf UMLS concept or said test data cannot be better classified to any children of the current UMLS concept.

DETAILED DESCRIPTION OF THE PREFERRED EMBODIMENTS

Figure 1:
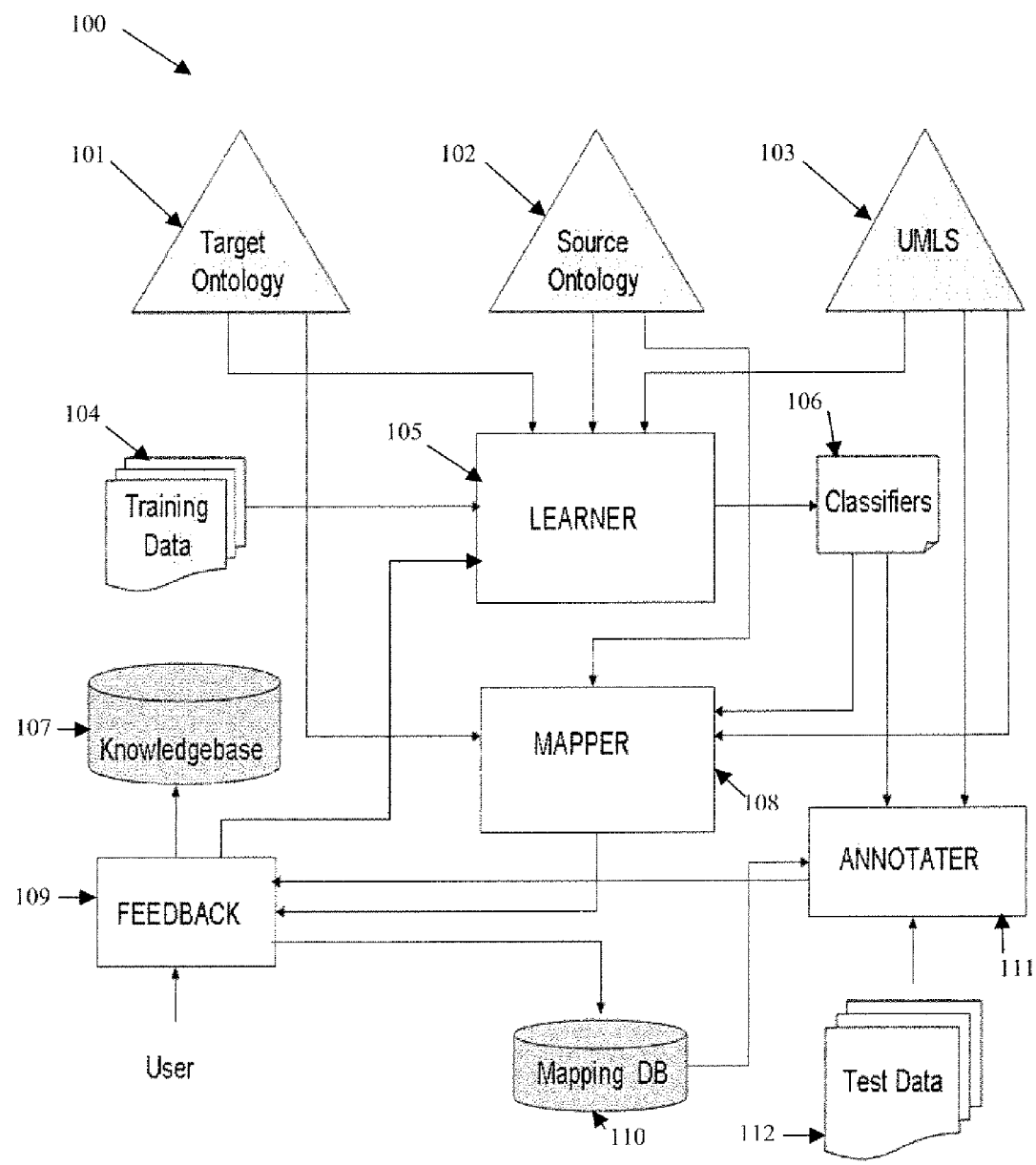
FIG. 1 is a block diagram of the system architecture of a medical information integration system according to an embodiment of the invention.

Exemplary embodiments of the invention as described herein generally include systems and methods for medical information integration. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

A medical information integration system according to an embodiment of the invention has been developed to combine content structuring as well as schema mapping into one integration framework, rather than being an effort in either data mediation or data warehousing. A content structuring module integrates unstructured text medical data to concepts from a target ontology. A schema integration module maps elements between a pair of heterogeneous biological data source schemas or ontologies. The content structuring module is primarily utilized when data is unstructured and non-schematic, while in the presence of structured data but with a nonstandard schema the schema integration module becomes important. Both these modules are driven by the use of a global knowledge base and learning algorithms characterized by limited training. Systems and methods according to embodiments of the invention can create structured content from unstructured data to produce machine-readable content which enables the development of automated and cost-efficient solutions to clinical health care problems. Furthermore, representing the structured content in terms of standard schemas provides for easy interoperability.

A medical information integration system according to an embodiment of the invention makes use of the Unified Medical Language System (UMLS) as a source of global knowledge. The UMLS provides an extensive umbrella vocabulary and taxonomy of terms in the medical domain. Very often, the target ontology being used in the content structuring process has a mapping to UMLS. In such situations, machine learning algorithms are used to exploit the mapping as well as the knowledge structure in UMLS. In particular, rather than train classifiers for only individual concepts in the target ontology, classifiers are trained also for corresponding UMLS concepts. The benefit of this approach is that the historical training data for UMLS concepts, as well as the extensive vocabulary of terms associated with them, can be leveraged upon during the training process. Furthermore, the taxonomic arrangement of concepts in UMLS is used to perform hierarchical classification. This is useful when the target ontology is not modeled as taxonomy, for instance the Logical Observation Identifiers Names and Codes (LOINC) for describing laboratory test results. In situations where mappings from target ontologies to UMLS do not exist, schema integration techniques are used to learn such mappings.

A philosophy behind the learning techniques in of a medical information integration system according to an embodiment of the invention is the use of minimal training effort. An effect of limited training is the lack of sufficiently labeled data for the lower level concepts of UMLS. However, higher level concepts are comparatively data rich due to the accumulation of data instances from their descendants. A medical information integration system according to an embodiment of the invention draws upon recent work on parameter estimation using shrinkage in a hierarchy of classes to improve the classifier parameters of the lower level concepts. Yet another effect of limited training is the presence of ambiguously labeled words in the data. Work on multiple instance learning focuses on the use of ambiguous training data for classifier learning. A medical information integration system according to an embodiment of the invention uses multiple instance learning techniques to train in the presence of ambiguous data. Realizing that learning algorithms can often produce incorrect associations, more so when trained with limited data, relevance feedback in the form of user correction is included with the integration process. Associations which fall beneath a level of certainty are ranked and the most ambiguous ones are presented to the user for correction. The results from the correction are incorporated into the system for better training. The system architecture of a medical information integration system according to an embodiment of the invention and its individual components are outlined and elaborated upon below.

FIG. 1 illustrates the architecture of a medical information integration system according to an embodiment of the invention. System 100 includes as components a learner 105, a mapper 108, an annotater 111, and a feedback module 109. As outlined before in the introduction, a feature of medical information integration system according to an embodiment of the invention is the use of both knowledge extraction and schema integration techniques within a single system. Knowledge extraction tasks are driven by a target ontology and the UMLS while schema integration is performed in the presence of both target and source ontologies aided by the knowledge in the UMLS.

The learner module 105 takes as input the target ontology 101, the source ontology 102, the UMLS 103, and training data 104 for concepts in all of them and outputs a set of classifiers 106 for the concepts in these ontologies. The schema integration tasks are carried out in the mapper module 108, which takes as input the source 102, target 101, and the UMLS 103 ontologies and the classifiers 106 from the learner module and generates and outputs associations between elements of these ontologies. These associations can be saved in a mapping database 110. The annotator module 111 performs knowledge extraction on test data 112 using the UMLS 103 and target ontology classifiers 106 and the mappings from the mapping database 110. The results from both the mapper module 108 and the annotater module 111 are fed through a feedback loop in the feedback module 109 for user corrections from users. The corrected results from feedback module are incorporated into a knowledge database 107 or into the mapping database 110, as appropriate, and can be supplied to the learner module 105 to improve the classifiers.

The learner module 105 performs the function of learning classifiers for concepts in the UMLS 103 and target ontology 101. During schema mapping, the UMLS classifiers 106 are used to map elements between the source 102 and target 101 ontologies while during knowledge extraction the UMLS and target ontology classifiers 106 are used to annotate the test data 113 with their respective concepts.

Figure 7:
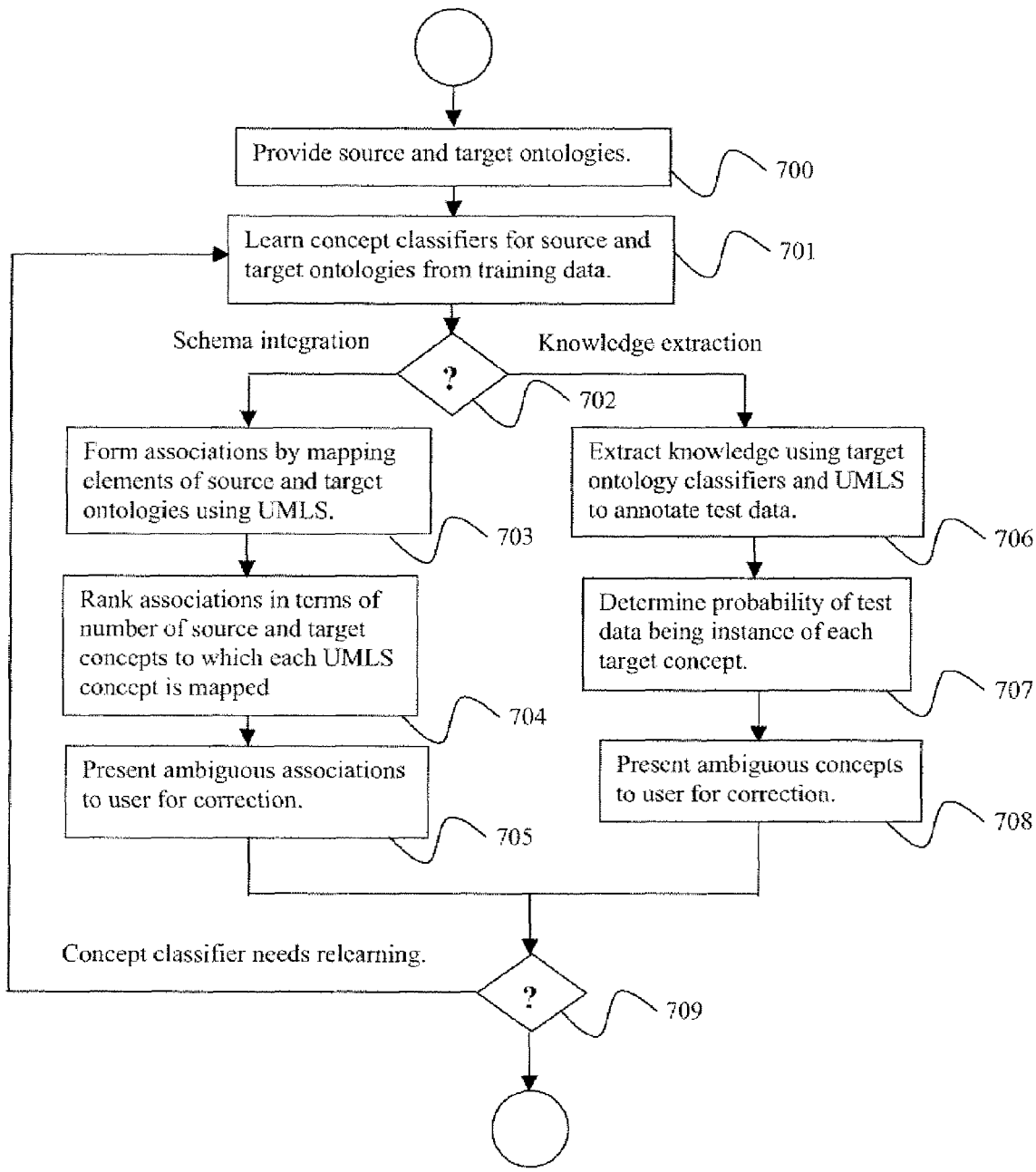
FIG. 7 is a flow chart of a medical information integration process, according to an embodiment of the invention.

A flow chart of medical information integration process according to an embodiment of the invention is depicted in FIG. 7. Referring now to the flow chart, source and target ontologies are provided at step 700. Concept classifiers for these ontologies are learned using training data at step 701. At step 702, it is determined whether schema integration or knowledge extraction is being performed.

For schema integration, the process proceeds to step 703, where association are formed by mapping elements between the source and target ontologies using the UMLS, and between the target ontology and UMLS. At step 704, the associations are sorted and ranked according to a degree of ambiguity as measured by a of source and target ontology concepts to which each UMLS concept is associated. The most ambiguous associations are presented to a user for correction of the underlying concept classifiers at step 705.

For knowledge extraction, the process proceeds to step 706, where the target ontology classifiers and the UMLS are used to annotate test data items with their respective concepts. At step 707, the probability of each test data item of being an instance of each target ontology concept is calculated, and the most ambiguous concepts are presented to a user for correction at step 708. If, at step 709, the user has determined that the association or test data annotations need correcting, the process returns to step 701 to retrain the appropriate concept classifiers.

In the following, a concept is defined as an abstract notion while an instance of a concept grounds the abstract notion. For instance, a concept could be "heart disease" while an instance of this concept could be "sclerosis of the arteries". Data entities are strings of words (such as "sclerosis of the arteries", "inflammation of the lungs") which are being classified to ontology concepts. Classification is a process which takes the classifier of a concept and a data entity and returns a quantitative value which is proportional to the likelihood of the data entity being an instance of the concept. If the value is above a threshold (which is set before the process is begun) then the data entity is said to be an instance of the concept. The classifiers of the concepts are learned in the learner module.

The learner module 105 uses two machine learning techniques for improved parameter estimation in the presence of limited training. Multiple instance learning is used to model training data for those concepts that contain words with a varying degrees of relevance that result from the limited training effort. The concept classifiers can be learned using any standard algorithm as is known in the art, e.g. Expectation Maximization with Diverse Density. Shrinkage of a class hierarchy is used to refine the parameters of lower level concepts using values from higher level concepts. This compensates for that fact that in a hierarchical learning setting, data at the lower level concepts is sparser compared to higher level concepts. The learner module 105 uses parametric Naïve Bayesian classifiers as learners.

Figure 2:
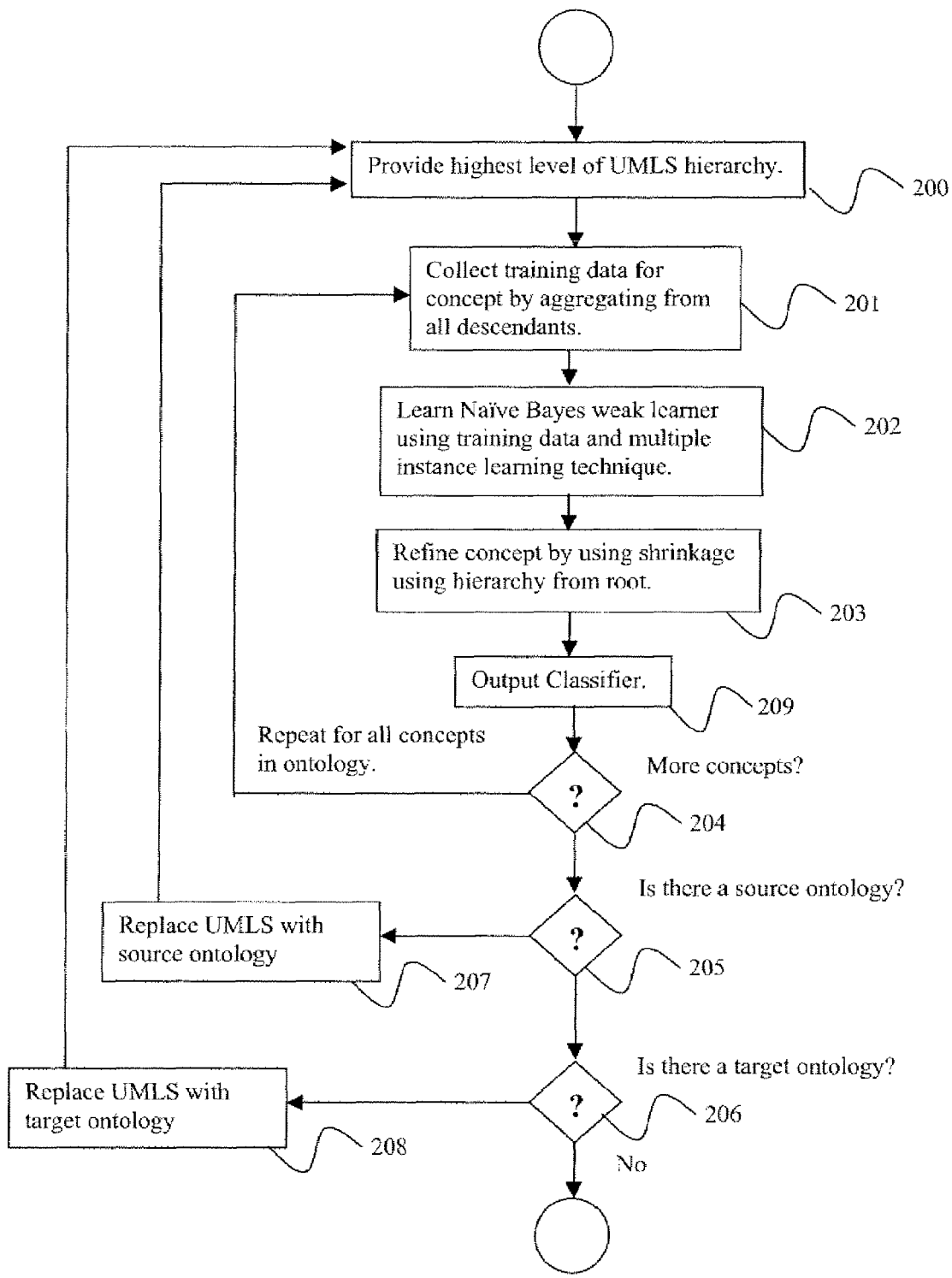
FIG. 2 is a flowchart of a learner module of a medical information integration system according to an embodiment of the invention.

A flowchart of a learner module of a medical information integration system according to an embodiment of the invention is shown in FIG. 2. Referring now to the flowchart, the learner starts with the root concept of the UMLS ontology at step 200. At step 201, the training data for the concept is created by aggregating the training data from all descendant concepts of the root UMLS concept in the ontology. At step 202, the training data is used to learn a Naïve Bayes classifier for the root UMLS concept. Since the training data is labeled with multiple concepts, techniques from multiple instance learning are used in this step. The learned classifier is improved at step 203 using shrinkage from the root of the ontology to the concept. The process is repeated for all the concepts in the ontology at step 204. At steps 205 and 207 the process is executed for source ontology concepts if such an ontology exists. Similarly, at steps 206 and 208 the process is executed for target ontology concepts if such an ontology exists. Each concept classifier is output at step 209.

A mapper module according to an embodiment of the invention generates mappings between elements of source and target ontologies during schema integration. The mapper module uses the UMLS as the mediated schema to derive mappings between source and target ontologies. Thus, concepts in the source and target ontologies are mapped to UMLS concepts separately first and then those which have been mapped to the same UMLS concept are mapped to each other. The mapper assumes the existence of data instances of the concepts of the ontologies being mapped. In the absence of a source ontology, the module maps only the target ontology to the UMLS. This target ontology to UMLS mapping is used during the knowledge extraction process (annotater module) if such a mapping did not already exist.

Figure 4:
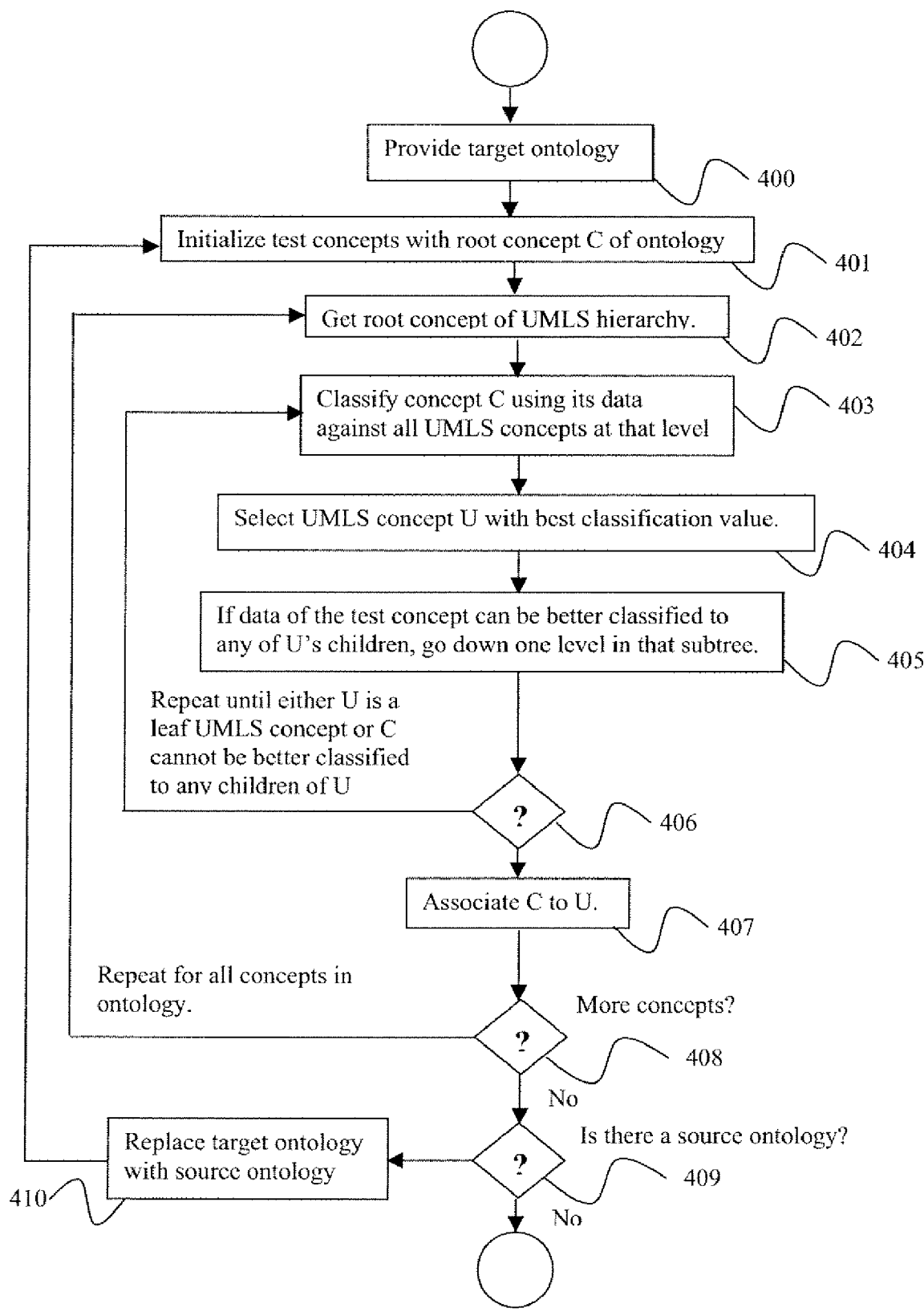
FIG. 4 is a flowchart of a mapping process according to an embodiment of the invention.

A flowchart of a mapping process according to an embodiment of the invention is shown in FIG. 4. Referring now to the flowchart, the mapping starts with the target ontology at step 400. At step 401, a test concept C is initialized with the root concept of the target ontology, and at step 402, the root concept of the UMLS hierarchy is provided as a current UMLS concept. At step 403, concept C is classified, using its data, against all UMLS concepts at the level of the current concept. At step 404, the UMLS concept U with the best classification value is selected. If, at step 405, the test data associated with test concept C can be better classified to any of U's children, the subtree corresponding to that child node of U is selected. The process loops at step 406 to repeat steps 403, 404, and 405 until either U is a leaf UMLS concept or C cannot be better classified to any children of U. Concept C is associated to U at step 407. The process loops at step 408 to repeat steps 402 to 407 for all concepts in the target ontology. At step 409, if there is a source ontology, the target ontology is replaced with the source ontology at step 410, and steps 401 to 408 are repeated. The result of a mapping process according to an embodiment of the invention is that concepts in the target and source ontologies are associated with UMLS concepts. For schema integration, source and target ontology concepts mapped to the same UMLS concept are returned as associations. For knowledge extraction, the mapping of the target ontology to the UMLS is used by the annotater module.

An annotater module according to an embodiment of the invention performs the task of associating test data to target ontology concepts. The UMLS classifiers, the target ontology classifiers trained by the learner module, and the hierarchical structure of UMLS are used to derive the annotations. The annotater module assumes that the target ontology has been mapped to the UMLS and that each UMLS concept is associated with a set (possibly empty) of target ontology concepts.

Figure 5:
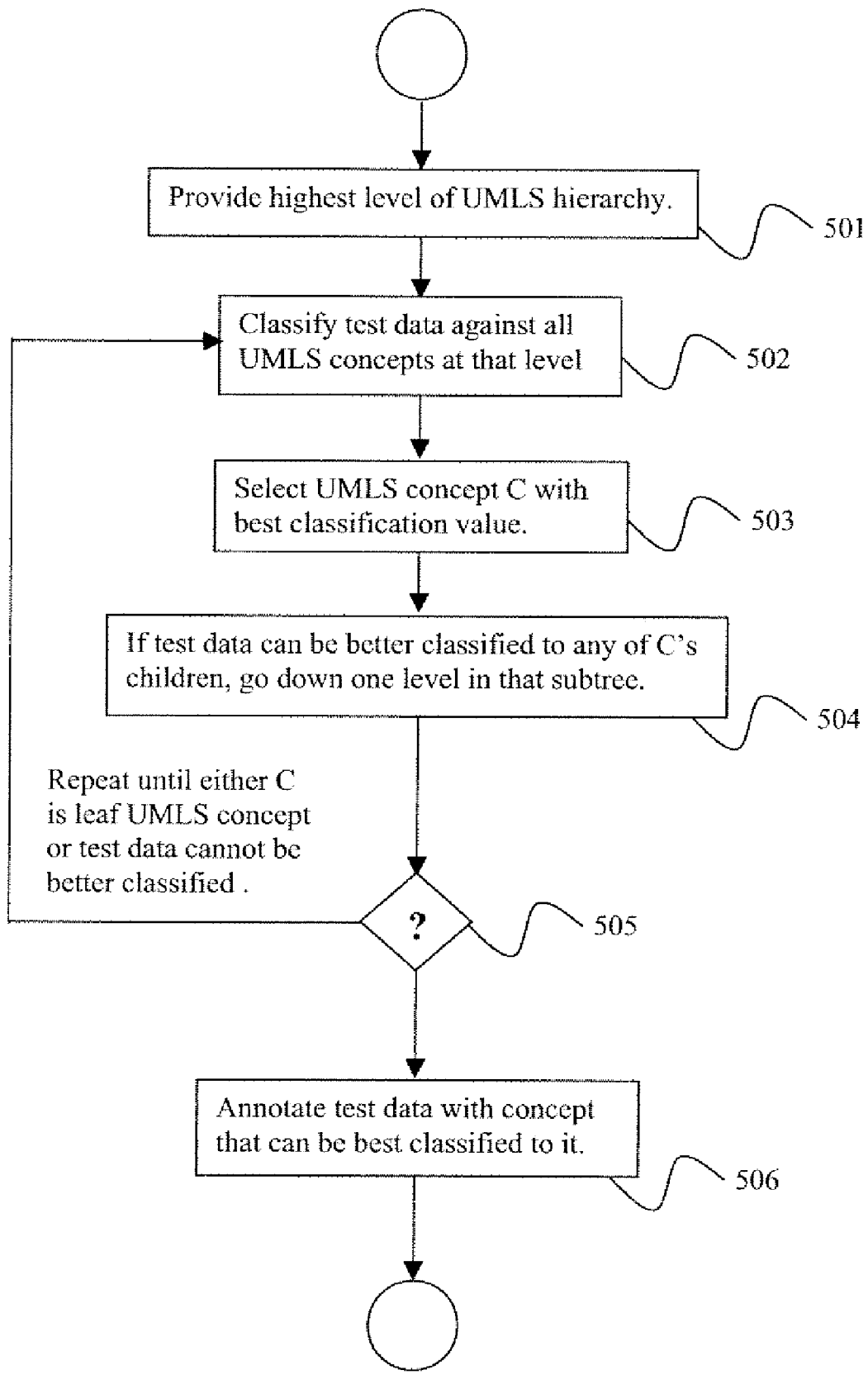
FIG. 5 is a flowchart of an annotation process according to an embodiment of the invention.

A flowchart of an annotation process according to an embodiment of the invention is shown in FIG. 5. Referring now to the flowchart, the annotator process starts at step 501 at the highest level of the UMLS hierarchy which has been mapped to the target ontology. Test data is classified at step 502 against all the UMLS concepts in that level which are associated with the target ontology. At step 503, the UMLS concept, C, with the best classification value, is selected. At step 504, if the test data can be better classified to any of C's children, go down one level in that subtree. The process loops at step 505 to repeat steps 502, 503, and 504 until either C is a leaf UMLS concept or the test data cannot be better classified to any children of C. At step 506, the test data is annotated with the concept which can be best classified to it among all the target ontology concepts associated with C.

A knowledge extraction or schema integration process according to an embodiment of the invention is improved by following a semi-automated approach. To that end, the feedback module incorporates relevance feedback from a user during knowledge extraction as well as during schema mapping. User feedback has been investigated within the context of schema integration in the prior art. However, the feedback in a medical information integration system according to an embodiment of the invention improves upon existing approaches by automatically providing the most ambiguous associations to the user instead of letting the user peruse all associations to decide the ambiguous ones.

During schema mapping, for each UMLS concept C, let $|S|_C$ and $|T|_C$ be, respectively, the number of source and target concepts to which it is mapped. Then, $|S|_C \times |T|_C$ represents the number of possible ambiguous mappings in C. The UMLS concepts are ranked in terms of decreasing $|S|_C \times |T|_C$ values and the concepts with the k highest values are presented to the user for correction. The user corrected mapping is stored in the mapping database. During knowledge extraction, P(T|test_data), the probability of the test data being an instance of concept T, is computed for every concept T in the target ontology. If the difference between the P(T|test_data) values of the best and the second best concepts is below a threshold, then the association is deemed ambiguous and is given to the user for correction The user corrected association is stored in the mapping database. The user's feedback is also incorporated as examples for retraining the relevant UMLS and the target ontology concepts during knowledge extraction.

Figure 3:
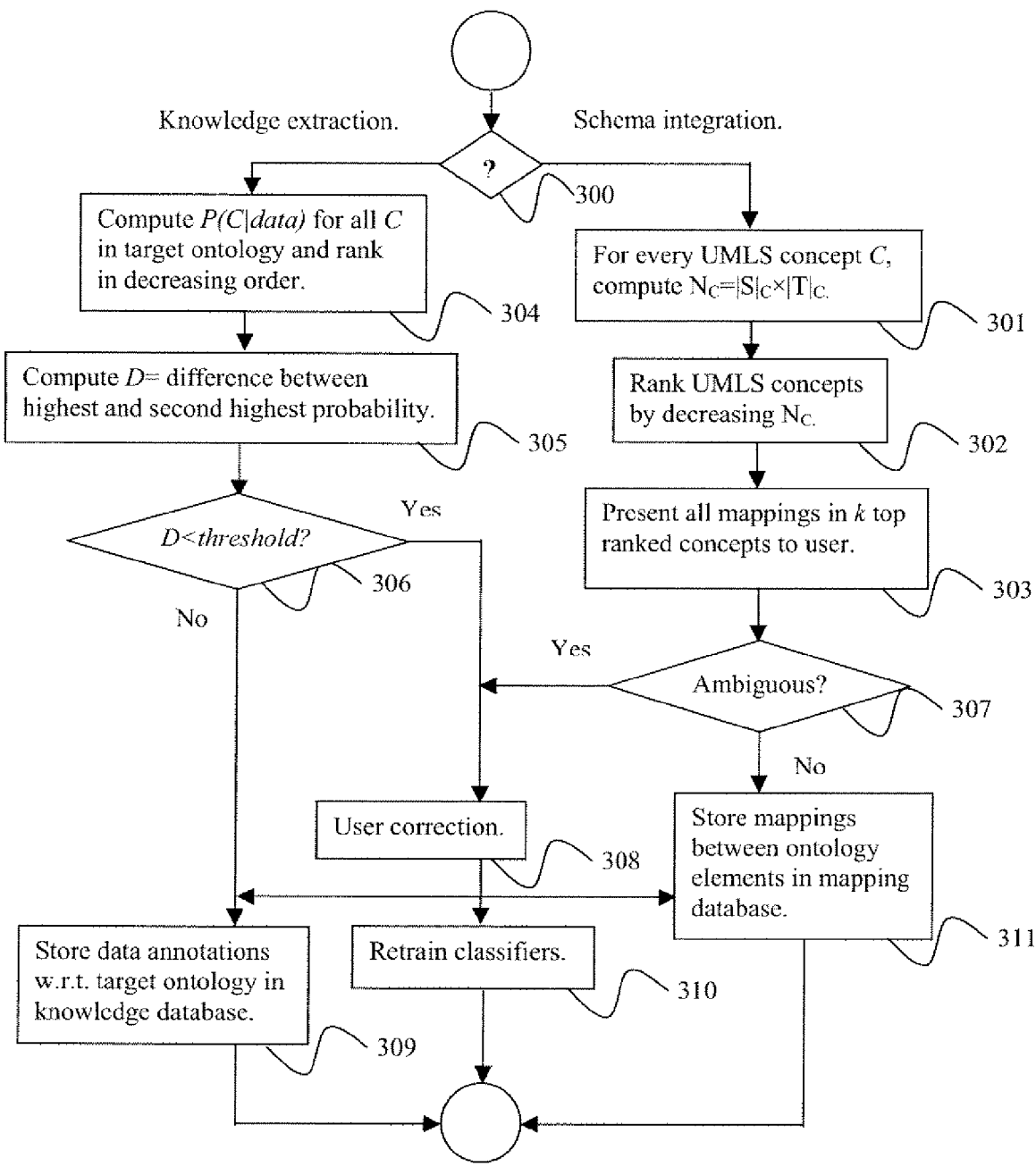
FIG. 3 is a flowchart of a feedback process of a medical information integration system according to an embodiment of the invention.

A flowchart of a feedback process of a medical information integration system according to an embodiment of the invention is illustrated in FIG. 3. Referring now to the flowchart, at step 300, it is determined whether the feedback is needed for schema integration or for knowledge extraction. For scheme integration, at step 301, the number of possible ambiguous mappings for each UMLS concept C, $NC = |S|_C \times |T|_C$, is computed. The UMLS concepts are ranked by decreasing $N_C$ at step 302. At step 303, all mappings in the k top ranked concepts are presented to a user, who will determine which of the associations is ambiguous at step 307. Those mappings between ontology elements that are not deemed ambiguous are stored at step 311 in the mapping database.

For knowledge extraction, the probability P(C|data) for all concepts C in the target ontology is computed and ranked in decreasing order at step 302. At step 303, the difference D between the highest ranked probability value and second highest probability value is computed. If, at step 306, this difference D is above a threshold, the association is not ambiguous, and data annotations with respect to the target ontology are stored in the knowledge database.

If, however, an association or UMLS concept are deemed ambiguous, the association is presented to a user for correction at step 308, and the classifiers are retrained at step 310.

It is to be understood that the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 6:
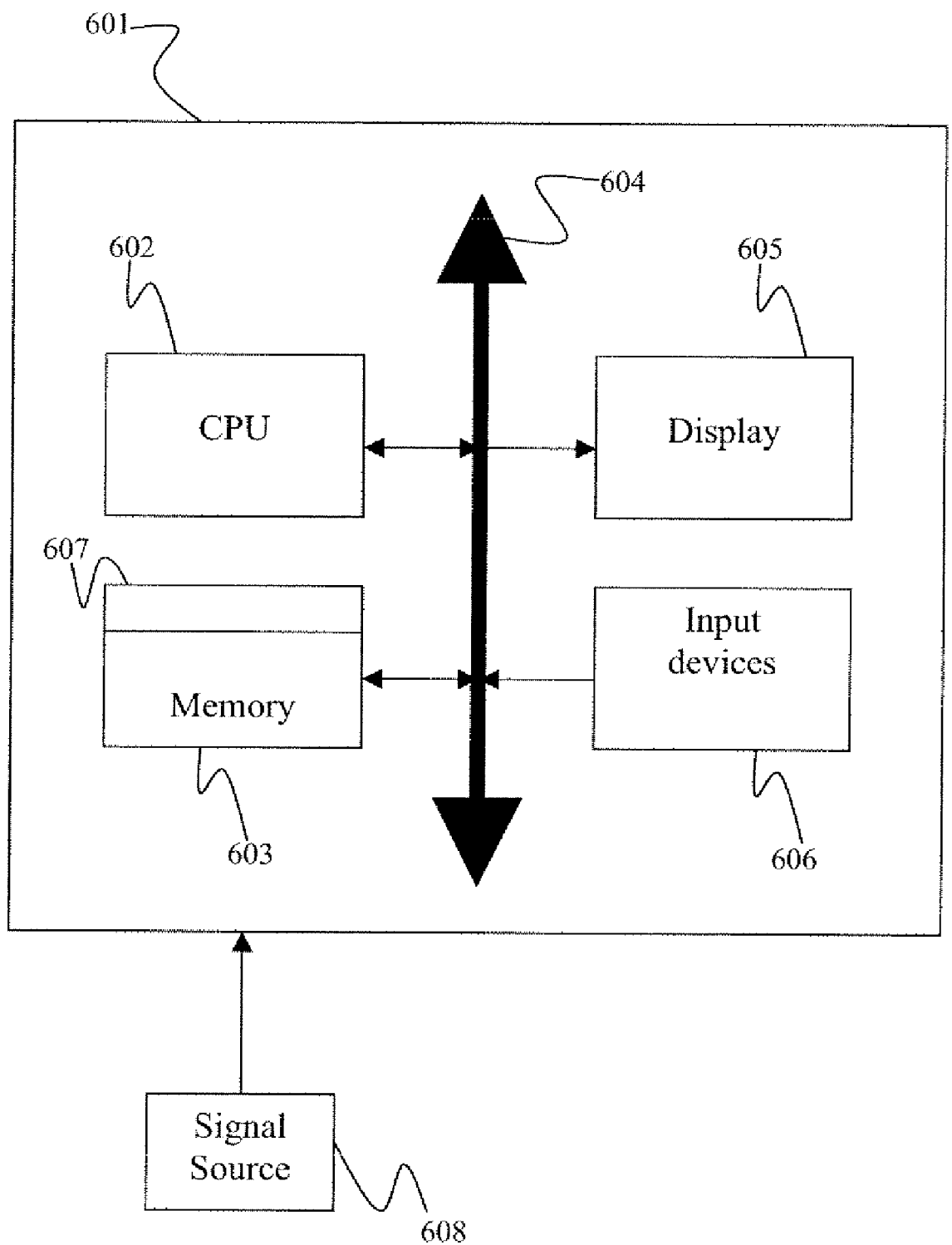
FIG. 6 is a block diagram of an exemplary computer system for implementing a medical information integration process according to an embodiment of the invention.

FIG. 6 is a block diagram of an exemplary computer system for implementing a medical information integration system according to an embodiment of the invention. Referring now to FIG. 6, a computer system 601 for implementing the present invention can comprise, infer alia, a central processing unit (CPU) 602, a memory 603 and an input/output (I/O) interface 604. The computer system 601 is generally coupled through the I/O interface 604 to a display 605 and various input devices 606 such as a mouse and a keyboard. The support circuits can include circuits such as cache, power supplies, clock circuits, and a communication bus. The memory 603 can include random access memory (RAM), read only memory (ROM), disk drive, tape drive, etc., or a combinations thereof. The present invention can be implemented as a routine 607 that is stored in memory 603 and executed by the CPU 602 to process the signal from the signal source 608. As such, the computer system 601 is a general purpose computer system that becomes a specific purpose computer system when executing the routine 607 of the present invention.

The computer system 601 also includes an operating system and micro instruction code. The various processes and functions described herein can either he part of the micro instruction code or part of the application program (or combination thereof) which is executed via the operating system. In addition, various other peripheral devices can be connected to the computer platform such as an additional data storage device and a printing device. Note that said computer system can be implemented as a distributed computer system comprising a plurality of CPUs and a plurality of storage devices interconnected by a computer network such as a local area network (LAN) or a global network such as the Internet. In such a system said routine 607 can comprise a plurality of modules stored in different storage devices and each running on a different CPU.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A computer implemented method for integrating medical information using the Unified Medical Language System (UMLS) as a hierarchical tree-structured taxonomy of medical terms, comprising the steps of:
    providing a source ontology and a target ontology, said ontologies comprising formalizations of domain concepts associated with a medical terminological vocabulary, each concept being associated with data, each said ontology being distinct from the UMLS;
    learning concept classifiers for said source and target ontologies from training data;
    forming associations that map elements between the source and target ontology using the UMLS and said concept classifiers, wherein associated source ontology elements and target ontology elements are mapped to a same UMLS concept, wherein forming associations comprises the steps of:
    providing an ontology;
    initializing a test concept with a root concept of said ontology;
    initializing a current UMLS concept with a root concept of UMLS;
    classifying said test concept using the data associated with said test concept against all UMLS concepts at the hierarchy level of said current concept;
    selecting a best UMLS concept from said hierarchy level that has a best classification of said test concept;
    determining whether the data associated with said test concept can be better classified with any child concept of said best UMLS concept, wherein
    if said test concept cannot be better classified with any child concept of said best UMLS concept, associating said test concept to said best UMLS concept, and
    if said test concept can be better classified with a child concept of said best UMLS concept, reinitializing the current UMLS concept with said child UMLS concept that better classifies the data associated with said test concept, and repeating said steps of classifying said test concept, selecting a best UMLS concept, and determining whether the test data can be better classified with a child concept until either said current UMLS concept is a leaf UMLS concept or said test concept cannot be better classified to any children of the current UMLS concept;
    ranking said associations in terms of a number of source and target concepts to which each UMLS concept is mapped; and
    presenting a predefined number of highest ranked associations to a user,
    wherein the steps of providing a source ontology and a target ontology, learning concept classifiers, forming associations, ranking said associations, and presenting associations to a user, are performed by a computer processor.

2. The method of claim 1, wherein learning classifiers comprises the steps of:
    providing an ontology;
    starting from a root concept of said ontology,
        collecting training data for said concept of said ontology by aggregating said training data from all descendants in the ontology tree;
        using multiple instance learning to learn a Naive Bayes classifier for said concept;
        improving the classifier by using shrinkage along a path from the root of the ontology to said concept; and
        associating the learned classifier to the concept, wherein said steps of collecting training data, using multiple instance learning, improving the classifier, and associating the learned classifier to the concept are repeated for each concept in the ontology.

3. The method of claim 2, wherein said ontology is UMLS.

4. The method of claim 2, wherein said ontology is said target ontology.

5. The method of claim 2, wherein said ontology is said source ontology.

6. The method of claim 1, further comprising reinitializing said test concept to another concept in said ontology, and repeating said steps of initializing a current UMLS concept, classifying said test concept, selecting a best UMLS concept, and determining whether the test data can be better classified with a child concept until said test concept can be associated to a best UMLS concept.

7. The method of claim 1, wherein said ontology is the target ontology.

8. The method of claim 1, wherein said ontology is the source ontology.

9. The method of claim 1, wherein ranking said associations comprises the steps of determining, for each concept in UMLS, a product of a number of source ontologies and a number of target ontologies to which said UMLS concept is mapped by an association; and sorting said UMLS concepts in terms of decreasing product values, wherein said predefined number UMLS concepts with highest product values are selected.

10. The method of claim 1, further comprising the step of retraining those classifiers presented to said user that are selected by said user for correction.

* * * * *